(12) United States Patent
Hale et al.

(10) Patent No.: US 7,232,409 B2
(45) Date of Patent: Jun. 19, 2007

(54) METHOD AND APPARATUS FOR DISPLAYING ENDOSCOPIC IMAGES

(75) Inventors: Eric Lawrence Hale, South Pasadena, CA (US); Nathan Jon Schara, Pasadena, CA (US); Hans David Hoeg, Montrose, CA (US)

(73) Assignee: Karl Storz Development Corp., Goleta, CA (US)

( * ) Notice: Subject to any disclaimer, the term of this patent is extended or adjusted under 35 U.S.C. 154(b) by 258 days.

(21) Appl. No.: 10/718,434

(22) Filed: Nov. 20, 2003

(65) Prior Publication Data

US 2005/0113643 A1    May 26, 2005

(51) Int. Cl.
*A61B 1/04* (2006.01)
*G06T 15/20* (2006.01)

(52) U.S. Cl. .................... 600/118; 600/117; 600/476; 345/427

(58) Field of Classification Search ............... 600/101, 600/118, 117, 407, 476, 477; 382/128, 131; 345/419, 427
See application file for complete search history.

(56) References Cited

U.S. PATENT DOCUMENTS

| | | | |
|---|---|---|---|
| 3,572,325 A | 3/1971 | Bazell et al. ................... 128/6 |
| 3,880,148 A | 4/1975 | Kanehira et al. ............... 128/6 |
| 4,697,577 A | 10/1987 | Forkner .......................... 128/6 |
| 5,230,623 A | 7/1993 | Guthrie et al. ................. 433/72 |
| 5,307,804 A | 5/1994 | Bonnet ........................... 126/7 |
| 5,313,306 A | 5/1994 | Kuban et al. .................. 348/65 |
| 5,515,160 A * | 5/1996 | Schulz et al. ............. 356/241.1 |
| 5,531,227 A | 7/1996 | Schneider ................. 128/653.1 |
| 5,617,857 A | 4/1997 | Chader et al. ............ 128/653.1 |
| 5,623,560 A | 4/1997 | Nakajima et al. ........... 382/295 |
| 5,638,819 A * | 6/1997 | Manwaring et al. ......... 600/424 |
| 5,661,519 A | 8/1997 | Franetzki ........................ 348/66 |
| 5,677,763 A | 10/1997 | Redmond ....................... 356/73 |
| 5,704,897 A * | 1/1998 | Truppe ......................... 600/117 |
| 5,776,050 A * | 7/1998 | Chen et al. .................. 600/117 |
| 5,899,851 A | 5/1999 | Koninckx .................... 600/117 |
| 5,920,395 A | 7/1999 | Schulz ......................... 356/375 |
| 5,954,634 A | 9/1999 | Igarashi ....................... 600/109 |
| 5,976,076 A | 11/1999 | Kolff et al. .................. 600/166 |
| 5,995,108 A * | 11/1999 | Isobe et al. .................. 345/421 |
| 6,007,484 A | 12/1999 | Thompson ................... 600/173 |
| 6,097,423 A | 8/2000 | Mattsson-Boze et al. ..... 348/65 |
| 6,135,946 A * | 10/2000 | Konen et al. ................ 600/117 |
| 6,139,499 A * | 10/2000 | Wilk ........................... 600/443 |

(Continued)

FOREIGN PATENT DOCUMENTS

| | | |
|---|---|---|
| JP | 6269403 | 9/1994 |
| WO | WO 95/01749 | 1/1995 |
| WO | WO 01/22865 | 4/2001 |

*Primary Examiner*—John P Leubecker
(74) *Attorney, Agent, or Firm*—St. Onge Steward Johnston & Reens LLC

(57) ABSTRACT

A method is disclosed for displaying endoscopic images that includes three-dimensional surfaces, variable viewing points, directions, and orientations. A computer receives a captured endoscopic image. A virtual surface is defined in the computer with the captured image textured onto the virtual surface. A virtual viewing point, virtual viewing direction, and virtual viewing orientation are defined relative to the virtual surface. A rendered image of the virtual surface is then created. The rendered image is displayed to the user. Video is displayed on the virtual surface by updating the image texture with each new frame.

20 Claims, 8 Drawing Sheets

U.S. PATENT DOCUMENTS

| | | | |
|---|---|---|---|
| 6,167,296 A | 12/2000 | Shahidi | 600/427 |
| 6,283,918 B1* | 9/2001 | Kanda et al. | 600/441 |
| 6,371,909 B1 | 4/2002 | Hoeg et al. | 600/173 |
| 6,442,417 B1* | 8/2002 | Shahidi et al. | 600/429 |
| 6,443,894 B1* | 9/2002 | Sumanaweera et al. | 600/443 |
| 6,464,631 B1 | 10/2002 | Girke et al. | 600/109 |
| 6,471,637 B1 | 10/2002 | Green et al. | 600/109 |
| 6,500,115 B2 | 12/2002 | Krattiger et al. | 600/173 |
| 6,505,065 B1* | 1/2003 | Yanof et al. | 600/427 |
| 6,648,817 B2 | 11/2003 | Schara et al. | 600/173 |
| 6,663,559 B2 | 12/2003 | Hale et al. | 600/118 |
| 6,695,774 B2 | 2/2004 | Hale et al. | 600/173 |
| 2002/0045855 A1 | 4/2002 | Frassica | 604/109 |
| 2002/0099263 A1 | 7/2002 | Hale et al. | 600/117 |
| 2002/0161280 A1 | 10/2002 | Chatenever et al. | 600/112 |
| 2003/0016883 A1 | 1/2003 | Baron | 382/289 |
| 2004/0127769 A1 | 7/2004 | Hale et al. | 600/173 |
| 2004/0210105 A1 | 10/2004 | Hale et al. | 600/101 |
| 2005/0015005 A1* | 1/2005 | Kockro | 600/427 |
| 2005/0020883 A1 | 1/2005 | Chatenever et al. | 600/173 |
| 2005/0027167 A1 | 2/2005 | Chatenever et al. | 600/173 |
| 2005/0054895 A1 | 3/2005 | Hoeg et al. | 600/117 |
| 2005/0085718 A1* | 4/2005 | Shahidi | 600/424 |
| 2005/0228250 A1* | 10/2005 | Bitter et al. | 600/407 |

* cited by examiner

METHOD AND APPARATUS FOR DISPLAYING ENDOSCOPIC IMAGES

FIELD OF THE INVENTION

The present invention relates to systems and methods for displaying images and specifically to the display of endoscopic images for medical and industrial applications.

BACKGROUND OF THE INVENTION

Endoscopes are elongated devices used to visualize the insides of cavities. Originally, endoscopes were equipped with eyepieces for direct observation. Today many endoscopes are equipped with electronic cameras, such as CCD or CMOS image sensors. These sensors are used to capture images from the area viewed with the endoscope. Endoscopic imaging is the process of capturing images from internal structures and transmitting them to an external viewer.

FIG. 1 illustrates specific definitions related to image capture. An imaging device, in this case an endoscope 10, is pointed towards a surface to be viewed 12 in a viewing direction 14. A principal light ray 16 travels from a point 18 on the surface 12, to the endoscope 10, through the endoscope optics (not shown), and finally to an image sensor (not shown). Prior to being refracted inside the endoscope 10, any principal ray leaving a point on the surface 12 travels approximately towards a viewing point 20. The viewing point 20 is the point from which the view can be thought to have been obtained. A plane 22 can be thought to exist between the surface 12 and the endoscope 10, orthogonal to the viewing direction 14. At the intersection of the plane 22 with the principal ray 16, there exists a point 24 which corresponds to the point 18 on the surface 12. The collection of all such points defined by principal rays defines an image. This image is generally equivalent to the actual image received by the image sensor. Therefore an image can be thought of as existing on this plane 22, although the actual imaging plane is located elsewhere. The endoscope has a field of view 26. In this case, the field of view 26 is shown as rectangular, although it could have any shape. Portions of the surface 12 that lie within the field of view 26 make up a visible area 28. The viewing orientation is the rotational orientation of the view about the viewing direction 14. The viewing set is defined herein as the combination of the viewing point, the viewing direction, and the viewing orientation. The view is what is seen from the viewing set. Although defined in the context of endoscopy, this terminology is also applicable to all other viewing situations.

Generally, a viewing situation involves a three-dimensional surface. However, the captured image is only a two-dimensional entity in an image plane that is generally orthogonal to the viewing direction of the endoscope. The image generated at the image plane is typically displayed to the user as would be seen looking along the viewing direction of the endoscope from the endoscopic viewing point. For comparison, stereo-viewing endoscopes capture two slightly offset images which are used to provide the user with a three-dimensional image. However, they still only provide a view from the viewing point and in the viewing direction of the endoscope. Because the endoscope, the user, and the internal structure being examined exist in an actual three-dimensional world, tying the user to the viewing set of the endoscope limits the way information about the internal structure can be conveyed. The user will often desire to change the viewing set. With existing technology, the only option for the user is to move the endoscope. This is not always convenient or even possible. In these and other instances it would be useful for the user to be able to change the viewing set without changing the actual position of the endoscope. An alternative viewing set could provide a better perspective of the physical surface and give the user a better sense of the relative locations of viewed features. For example, it would be advantageous to be able to use a viewing set which is aligned with the user's physical position instead of the physical position of the endoscope. Other viewing sets might also be desired, as determined by the preferences of the user.

Two methods of volumetric image navigation are described in U.S. Pat. No. 6,167,296 to Shahidi and in U.S. Pat. No. 6,442,417 to Shahidi, et al. These methods both utilize a volumetric data set obtained in a preoperative X-ray or MRI scan to construct a three-dimensional anatomical model in a computer. This model is used to generate two-dimensional perspective projection views of the simulated anatomy. These views may then be compared with an actual endoscopic image. However, although these systems provide a three-dimensional model with a variable viewing set, they can only display the endoscopic image from the viewing set of the endoscope.

Because of this limitation, which is common for all existing endoscopic display systems, the true nature of the viewed area is often not conveyed adequately to the user. It would therefore be desirable to display the endoscopic image in a way that more accurately represents the actual three-dimensional surface from which the image was taken and permits the user to achieve a wide variety of different views of this surface.

Accordingly, the primary object of the present invention is to provide a versatile method of displaying endoscopic images that includes three-dimensional surfaces, variable viewing points, directions, and orientations. It is a further object of this invention to have this method applicable to all endoscopes regardless of type, viewing direction, or image sensor format.

BRIEF SUMMARY OF THE INVENTION

In accordance with the present invention, a method for displaying an endoscopic image comprises receiving an endoscopic image of a viewed surface, providing a virtual surface with said endoscopic image mapped onto said virtual surface, rendering a rendered image of said virtual surface, and providing said rendered image to a user.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what we presently believe is the best mode of carrying out the invention.

The preferred embodiment of the invention is a software program running on a computer. The computer communicates electronically with an endoscope and a display device such as a monitor. The computer includes a graphics processing unit such as those manufactured by NVidia Corporation. The graphics processing unit is specifically designed to quickly perform the types of graphics related calculations required by the present invention. Other devices may be connected to the computer as appropriate for a given application.

Figure 2A:
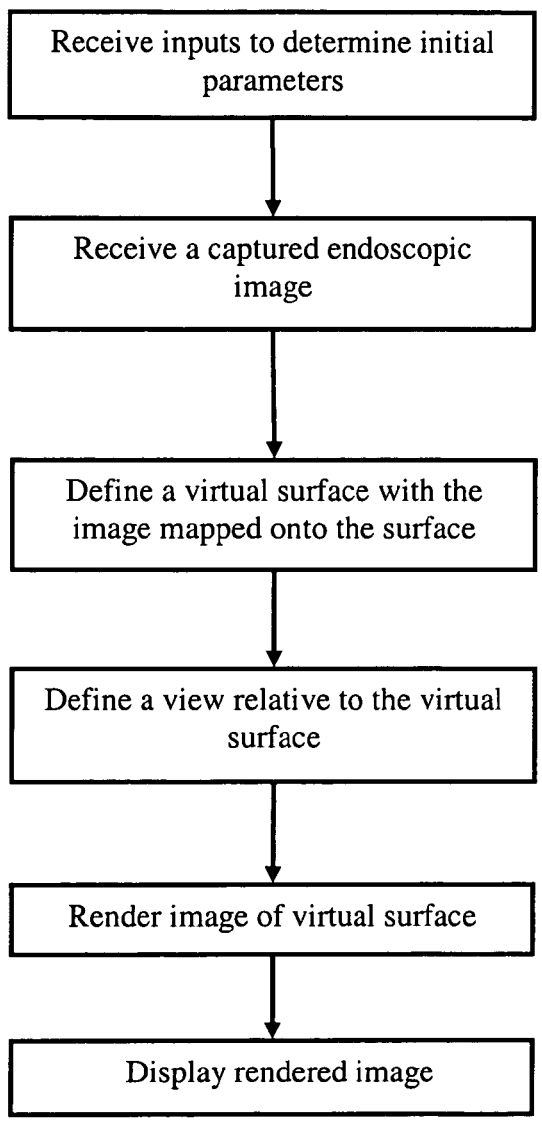
FIGS. 2A and 2B show the method of the present invention.

The program uses the graphical display programming library OpenGL. This library offers a powerful set of programming tools optimized for displaying textured shapes in three dimensions. It allows a collection of virtual shapes and a virtual viewing set to be defined as data within the computer memory. The collection of virtual shapes is then rendered based on the viewing parameters and displayed on a monitor. An alternative library, such as DirectX, could be used without departing from the scope of this invention FIG. 2A shows the method of the present invention for displaying an endoscopic image. First, the computer receives inputs to determine configuration parameters which are stored in memory. Second, the computer receives a captured endoscopic image. A virtual surface is defined in the computer with the image textured onto the surface. A virtual viewing point, virtual viewing direction, and virtual viewing orientation are defined relative to the virtual surface. A rendered image is then created using a perspective projection of the virtual surface as seen with the defined virtual viewing set. Alternatively, a parallel projection rendering could be used. The rendered image is then displayed to the user. Video is displayed on the virtual surface by updating the image texture with each new frame.

Figure 2B:
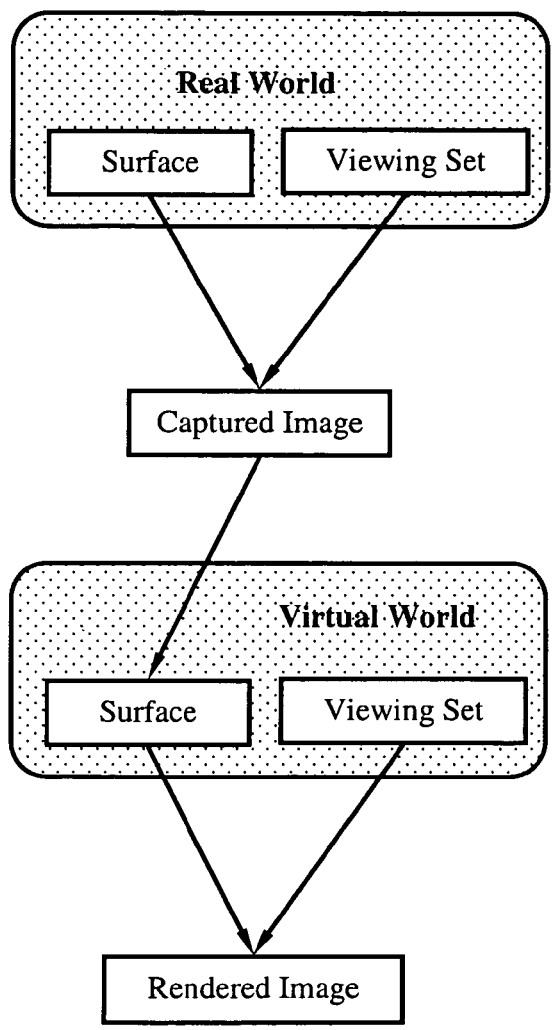

FIG. 2B conceptually illustrates the method of present invention. Given a real viewing set and a real surface, a captured image is provided by an endoscope. The captured image is mapped onto a virtual surface. The virtual surface and a virtual viewing set are then used to create a rendered image.

Figure 3A:
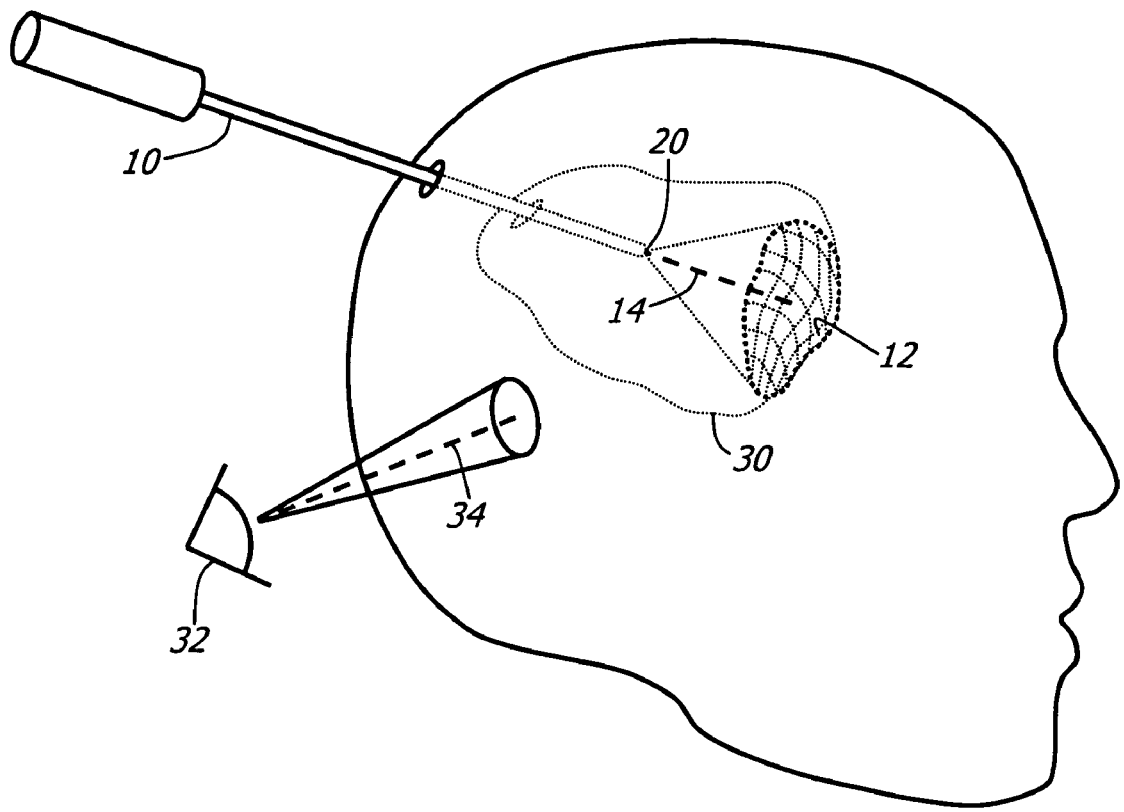
FIGS. 3A and 3B show a relationship between different views.
Figure 3B:
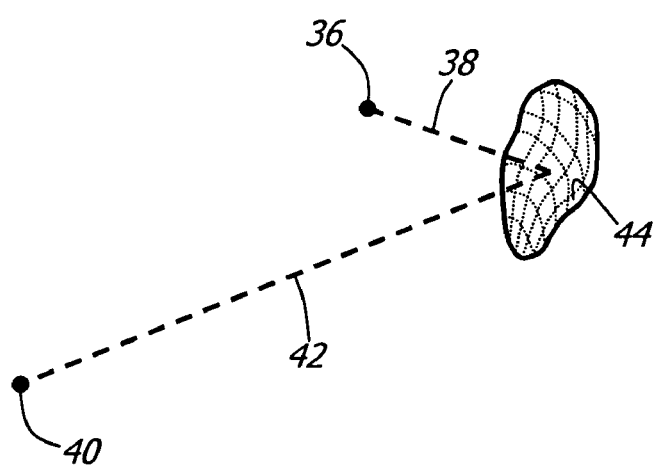

FIGS. 3A and 3B provide an example of the spatial relationship between different views. In FIG. 3A an endoscope 10 is positioned within a cavity 30 and captures an image of a surface 12. The endoscope 10 has a viewing point 20 and a viewing direction 14. A user has a viewing point 32 and a viewing direction 34 but is unable to see the surface 12. The virtual counterparts to this situation, as defined in the computer, are shown in FIG. 3B. The endoscopic viewing point 20 has a corresponding virtual endoscopic viewing point 36; the endoscopic viewing direction 14 has a corresponding virtual endoscopic viewing direction 38; the user viewing point 32 has a corresponding virtual user viewing point 40; and the user viewing direction 34 has a corresponding virtual user viewing direction 42. The captured endoscopic image is mapped onto a virtual surface 44 which approximates the real surface 12. Once the virtual surface 44 and the virtual user viewing set have been established, a new view is rendered and displayed. This rendered view is approximately what could be seen by the user if the surface were not occluded by the surrounding anatomy. In the computer defined world it is possible to pick any arbitrary viewing point, including points "behind" the virtual surface 44. This affords the user the ability to "see" the surface 12 from positions other than the endoscopic viewing point 20.

Figure 4A:
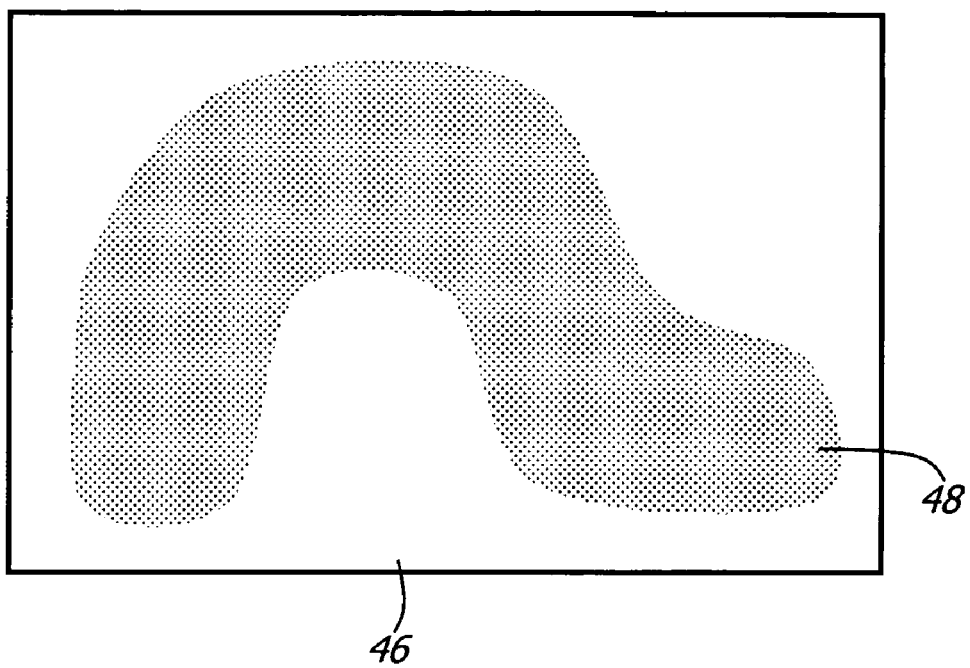
FIGS. 4A, 4B, 4C, and 4D show presentations of an endoscopic image of a surface.
Figure 4B:
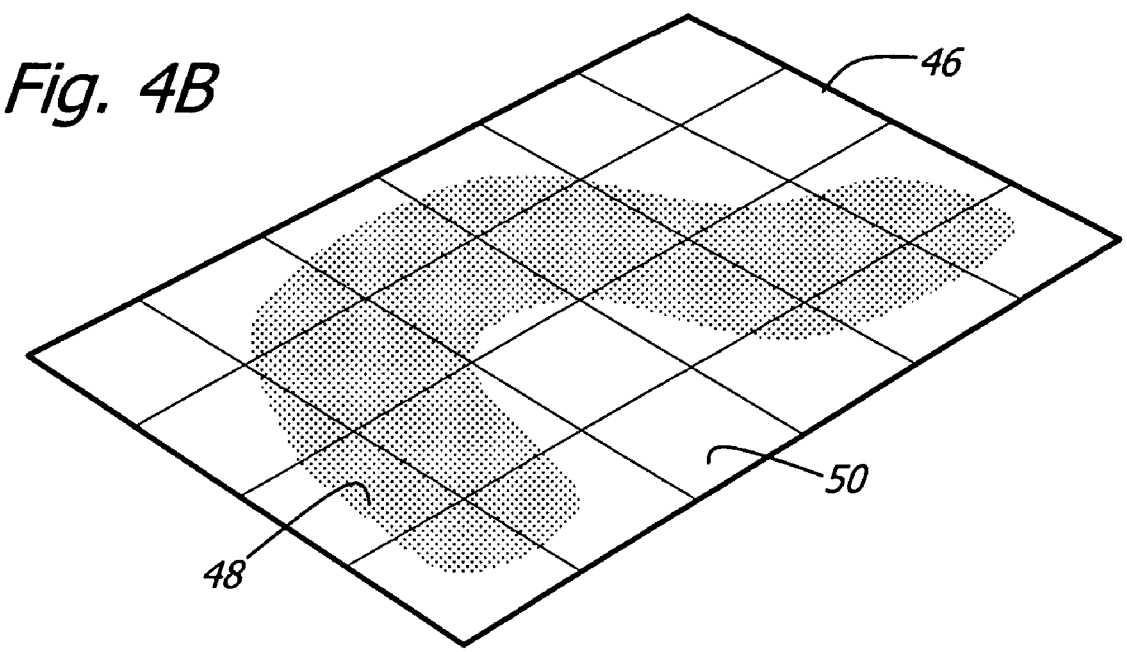
Figure 4C:
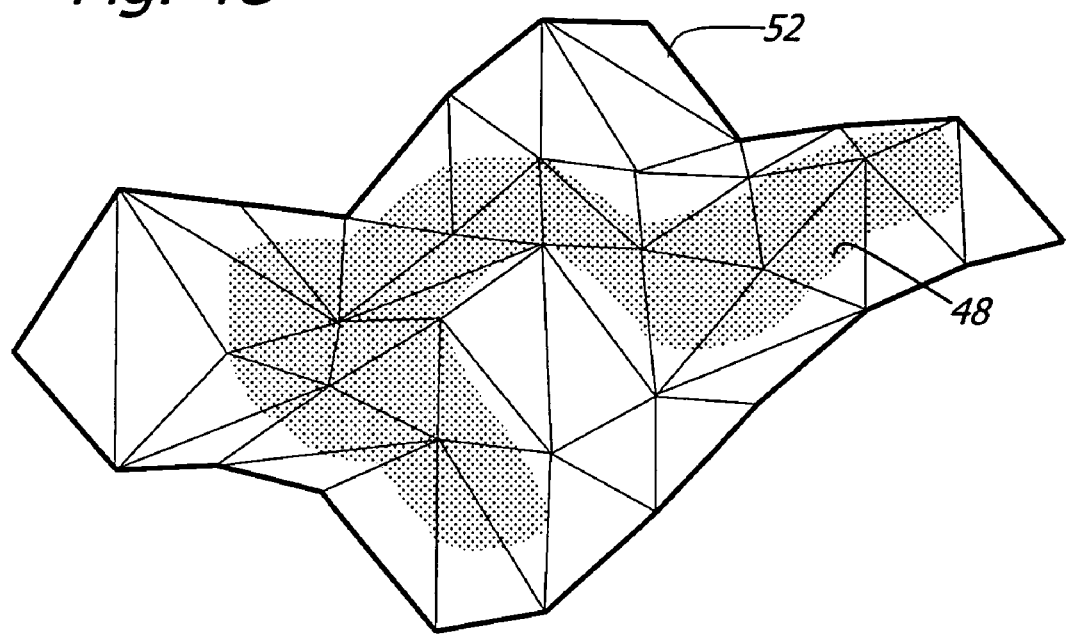
Figure 4D:
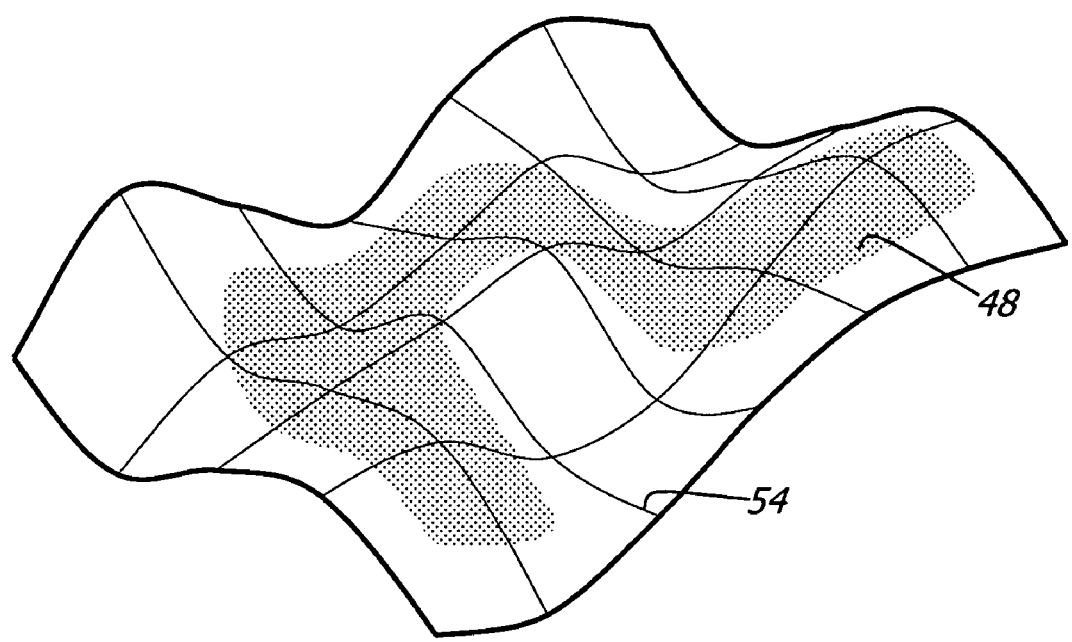

FIGS. 4A, 4B, 4C, and 4D show different presentations of an endoscopic image. FIG. 4A shows a captured endoscopic image 46 featuring a darker region 48. This is the standard presentation for an endoscopic image. FIG. 4B shows this same image 46 mapped onto a planar virtual surface 50 and seen from a different viewing point than that from which the image 46 was captured. Because of the alternative viewing point, the darker region 48 now appears to have been stretched and compressed in certain directions. A plane is the simplest surface available and is only a crude approximation of the real surface. However, a plane is a good choice when computing resources are limited. For a better approximation, polygons can be used to construct a three-dimensional virtual surface. Such a polygonal mesh could be based on selected points on an actual surface. Point coordinates may be obtained from a variety of sources including X-ray or MRI scans. FIG. 4C shows the endoscopic image 46 mapped onto a triangular mesh 52. The darker region 48 is stretched in accordance with the topography, giving the user a better sense of the actual geometry. An advanced system could provide a refined surface approximation, shown in FIG. 4D. Such an approximation could either be a high resolution volumetric data set or a mathematical function. In this case the darker region 48 appears smoother and more natural.

Figure 1:
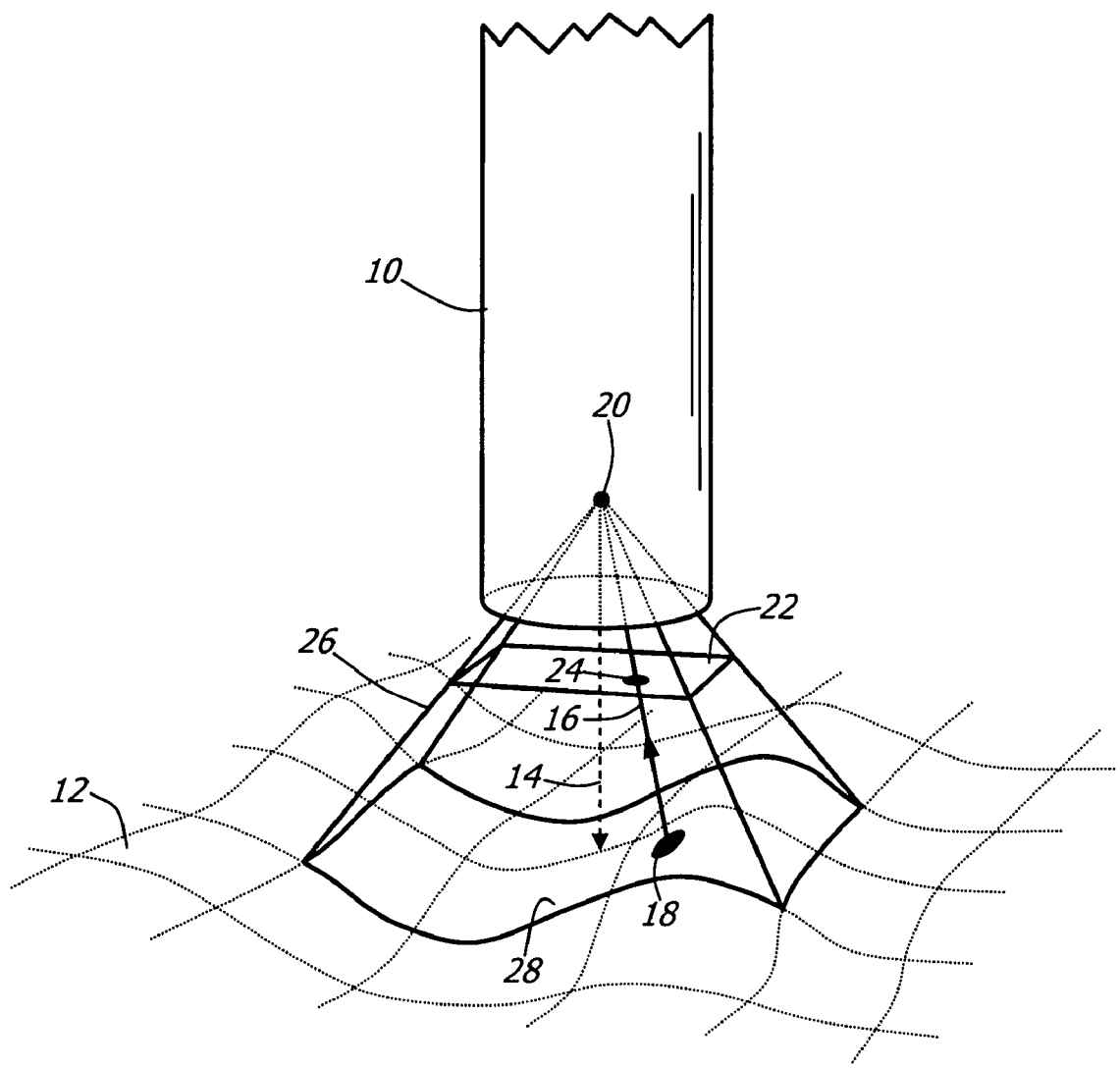
FIG. 1 shows an endoscope capturing an image.
Figure 5:
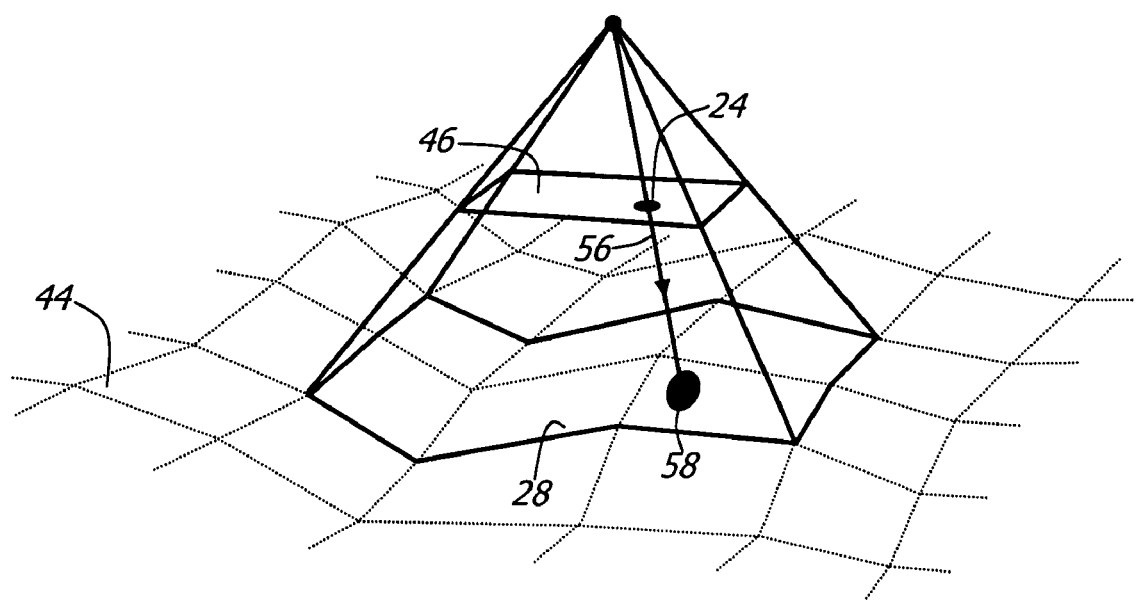
FIG. 5 illustrates the process of mapping an endoscopic image onto a virtual surface.

FIG. 5 shows conceptually how a captured image is mapped onto a virtual surface. This mapping process can be thought of as the inverse of the image capturing process. The virtual surface 44 is an approximation of the actual surface 14 shown in FIG. 1. A point 24 on the image 46 and a corresponding point 58 on the virtual surface 44 are matched along a projection line 56. The projection line 56 is analogous to the light ray 10. In the simplest case, the projection lines 56 connect corners of the image to the corresponding corners of the virtual surface. Intermediate projection lines 56 can be used to increase texturing accuracy on curved virtual surfaces. Some situations may require image distortion to be corrected by arranging the distortion lines 56 according to the inverse mapping of the distortion. Other specialized mappings may also be used without departing from the scope of the invention. The image 46 is textured onto the virtual surface 44 by fixing points on the image 46 to the corresponding points on the surface 44.

Figure 6A:
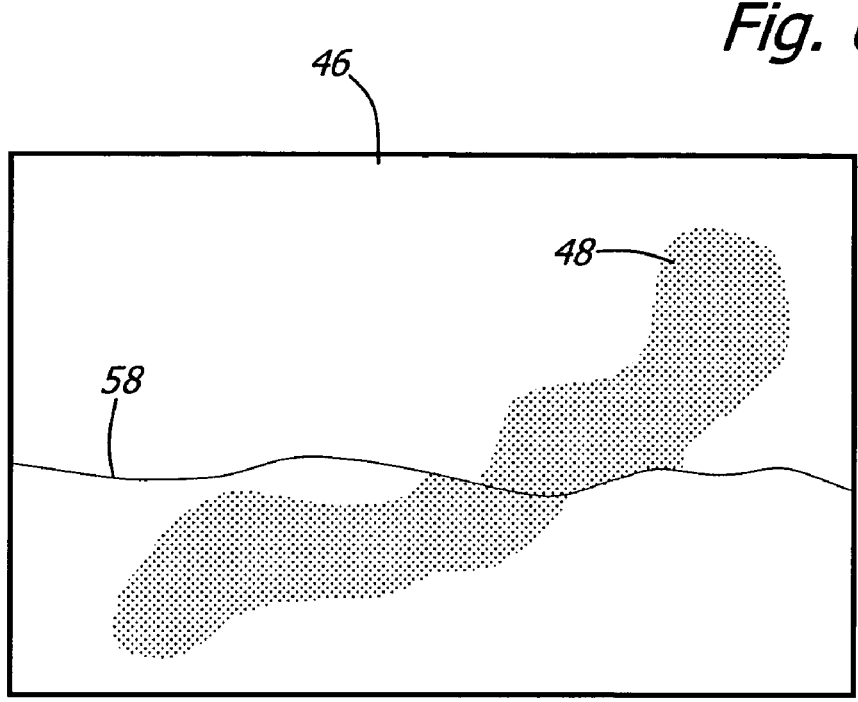
FIGS. 6A and 6B show presentations of an endoscopic image of a surface with a hidden region.
Figure 6B:
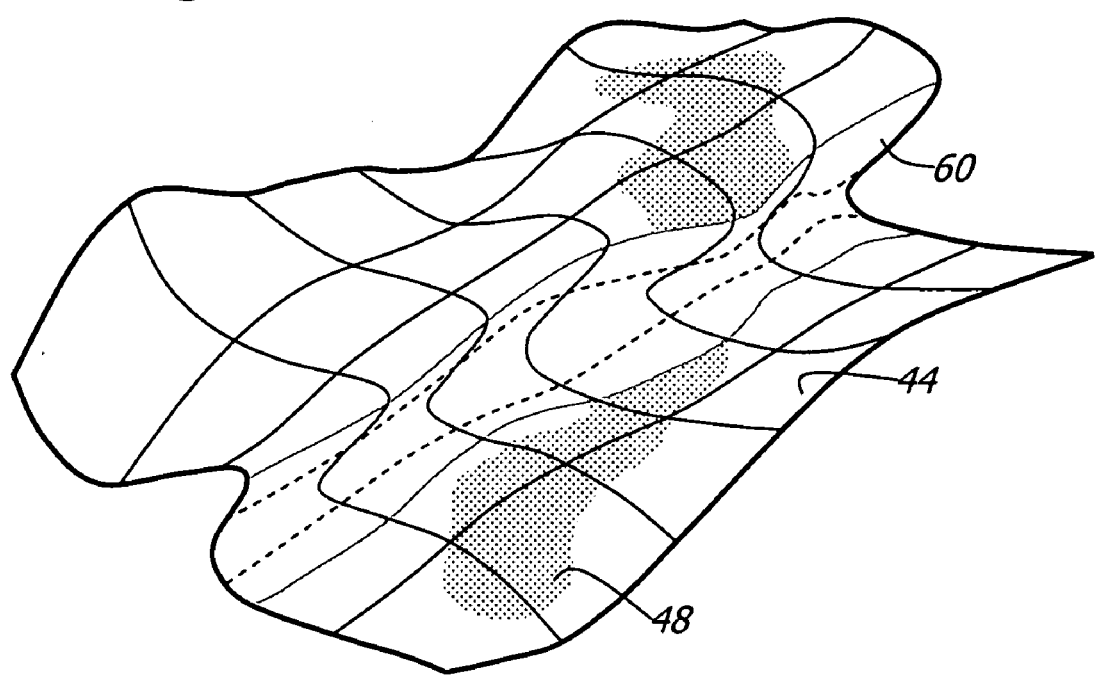

In certain cases the anatomy may be shaped in such a way that parts of it are obscured from the endoscopic viewing point. FIG. 6A shows an endoscopic image 46 of an imaged surface. It has a darker region 48 which appears broken. This discontinuity, along with an apparent contour line 58, suggests that the imaged surface may have hidden regions. FIG. 6B shows a virtual surface 44 with a folded region 60 that approximates the imaged surface. The folded region 60 is not visible from the endoscopic viewing point and therefore does not have any image data. Such regions may be indicated to the user by a solid color. Thus, even though there is no image information about these regions, the user can get a sense of surface geometry and how it relates to the image.

Figure 7:
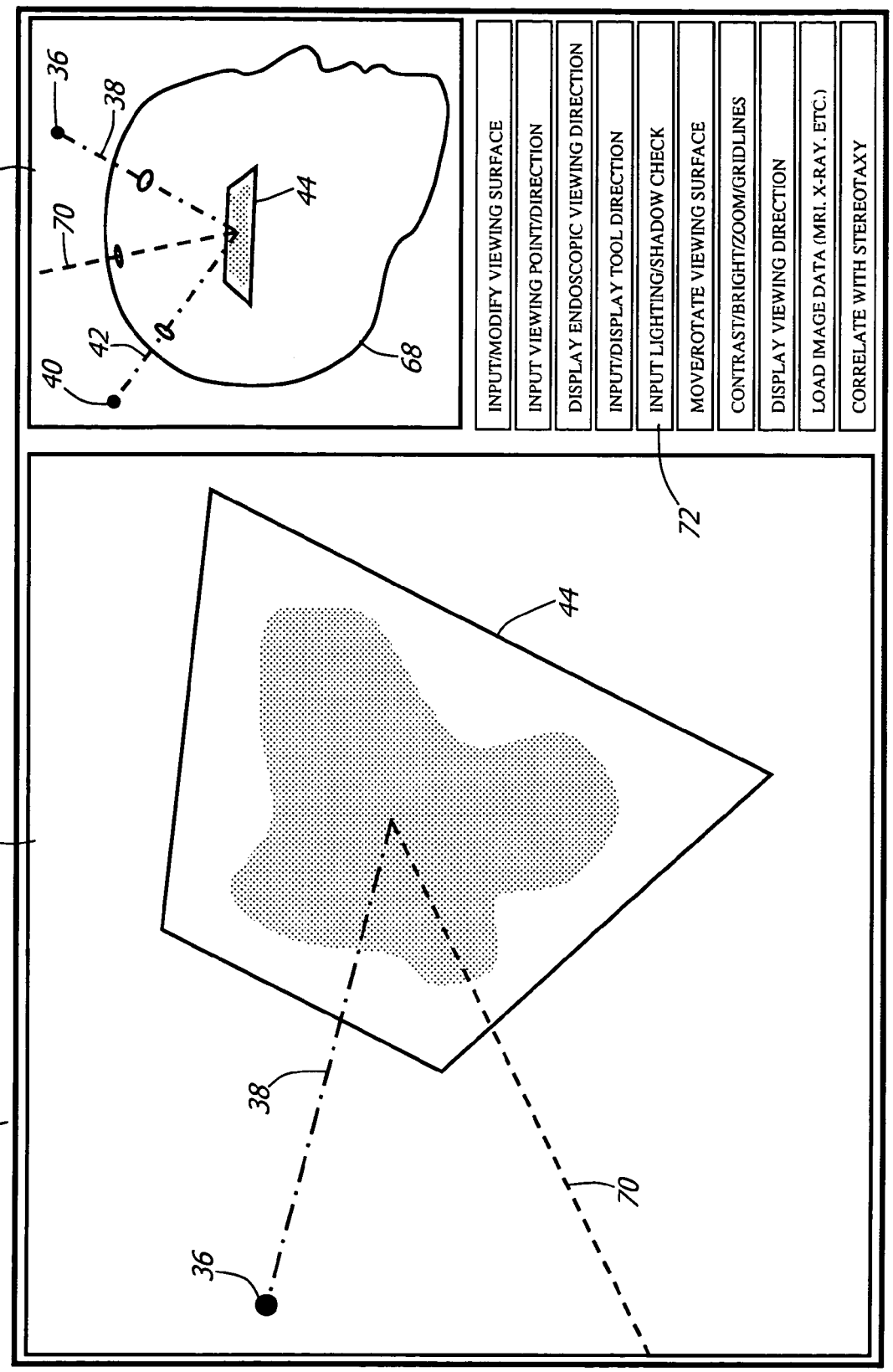
FIG. 7 shows the output of a display system according to the present invention.

FIG. 7 shows how the viewing information is displayed and how the user interacts with the virtual world. A large section 64 of a display screen 62 presents a view of a virtual surface 44 as seen from a selected viewing point. A smaller section 66 of the screen 62 gives an overview of the relative locations of the virtual endoscopic viewing point 36, a user selected viewing point 40, and the surface 44. An anatomical model 68 based imaging data or user input may also be displayed for clarity. Also shown is a tool line 70, which represents the line of action of an endoscopic surgical tool such as a cutter. The lower right corner of the display screen 62 presents a set of menu buttons 72 which allow the user to interact with the virtual world and also execute basic display and image processing/enhancement functions.

The configuration parameters required by the computer may be obtained in a variety of ways. For example the virtual surface can be constructed from scan data obtained through techniques such as MRI. Alternatively, the virtual surface could be selected from a collection of standard surfaces. The virtual viewing point, viewing direction, and viewing orientation may be specified using any standard data input technique. Specialized pointers for specifying the viewing set can also be used. The relationship between the endoscopic viewing set and the actual viewing surface can be input by the user or obtained from stereotactic systems or other sensors.

Accordingly, the present invention provides a new method for viewing endoscopic images which affords the user an enhanced, versatile, and more realistic representation of structures viewed by an endoscope.

The present invention has been described above in terms of a presently preferred embodiment so that an understanding of the present invention can be conveyed. However, there are many alternative modes of operation not specifically described herein but with which the present invention is applicable. For example, although specific surface approximation schemes were given, any surface approximation technique known from fields such as computer graphics and machine vision would fall under the scope of this invention. Also, there are many different ways to implement a user interface. In addition, while the examples were given with respect to endoscopes for use in surgical procedures, the present invention would be equally applicable with respect to borescopes or the like for use in non-medical situations. The scope of the present invention should therefore not be limited by the embodiments illustrated, but rather it should be understood that the present invention has wide applicability with respect to viewing instruments and procedures generally. All modifications, variations, or equivalent elements and implementations that are within the scope of the appended claims should therefore be considered within the scope of the invention.

We claim:

1. A method for providing images of a viewed surface to a user, the method comprising:
    moving an endoscope relative to a real surface which provides an endoscope view;
    using the endoscope to acquire an image of the real surface;
    providing a virtual surface approximating the topography of the real surface;
    mapping the acquired image onto the virtual surface;
    establishing a second viewing position relative to the real surface that represents a view different than the endoscope view;
    determining position data indicating the difference between the endoscope view and the view from the second viewing position as the endoscope moves;
    using the mapped virtual surface and the position data to render an image representing a view of the real surface from the second viewing position; and
    providing the rendered image to the user.

2. The method of claim 1, wherein at least the steps of using the endoscope to acquire an image, mapping the acquired image onto the virtual surface, and using the mapped virtual surface and the position data to render an image are repeated when the endoscope is moved relative to the real surface.

3. The method of claim 1, wherein the image is one of a series of video images.

4. The method of claim 1, wherein the topographical approximation is based on volumetric scan data.

5. The method of claim 1, wherein the topographical approximation is based on stereo imaging.

6. The method of claim 1, wherein the second viewing position represents the position of a user.

7. The method of claim 1, wherein the virtual surface represents an anatomical object.

8. The method of claim 1, wherein the virtual surface is planar.

9. The method of claim 1, wherein the position of the endoscope is represented by a first viewing set including a scope viewing point, a scope viewing direction, and a scope orientation relative to the real surface, and the second position is represented by a second viewing set including a virtual viewing point, a virtual viewing direction, and a virtual orientation corresponding to the second position.

10. The method of claim 1, wherein a virtual viewing point is arranged in a manner generally corresponding to an endoscopic viewing point.

11. The method of claim 1, wherein a virtual viewing point is arranged in a manner generally corresponding to an actual viewing point of a user.

12. The method of claim 1, wherein a virtual viewing direction is directed in a manner generally corresponding to an actual viewing direction of a user.

13. The method of claim 1, wherein a virtual viewing orientation is oriented in a manner generally corresponding to an actual viewing orientation of a user.

14. The method of claim 1, wherein the image is mapped onto the virtual surface according to a mapping that adjusts for distortion.

15. An apparatus for providing images of a viewed surface to a user, comprising:
    an endoscope providing an endoscope view that captures an image of a real surface when moved relative to the real surface;
    a processor that creates a virtual surface approximating the topography of the real surface, maps the image acquired by said endoscope onto the virtual surface, determines position data indicating the difference between the endoscope view and a view from a second viewing position relative the real surface different than the endoscope view as the endoscope moves, and uses the mapped virtual surface and the position data to render an image representing a view of the real surface from the second viewing position; and
    a monitor in communication with said computer that displays the rendered image.

16. The apparatus of claim 15, wherein, each time the endoscope acquires a new image, the processor maps the new image onto the virtual surface and uses the mapped virtual surface and the position data to render another image.

17. The method of claim 15 wherein the image is one of a series of video images.

18. A method for providing images of a viewed surface to a user, the method comprising:
   inserting an endoscope into a cavity;
   moving the endoscope relative to a real surface which provides an endoscope view;
   using the endoscope to acquire an image of the real surface;
   providing a virtual surface approximating the topography of the real surface;
   mapping the acquired image onto the virtual surface;
   establishing a second viewing position representing a view different than the endoscope view relative to the real surface;
   determining position data indicating the difference between the endoscope view and the view from the second viewing position as the endoscope moves;
   using the mapped virtual surface and the position data to render an image representing a view of the real surface from the second viewing position; and
   providing the rendered image to the user.

19. The method of claim 18 wherein at least the steps of using the endoscope to acquire an image, mapping the acquired image onto the virtual surface, and using the mapped virtual surface and the position data to render an image are repeated when the endoscope is moved relative to the real surface.

20. The method of claim 18, wherein the image is one of a series of video images.

* * * * *